United States Patent [19]

Cohen

[11] Patent Number: 5,146,926
[45] Date of Patent: Sep. 15, 1992

[54] METHOD AND APPARATUS FOR IMAGING ELECTRICAL ACTIVITY IN A BIOLOGICAL SYSTEM

[75] Inventor: Richard J. Cohen, Waban, Mass.

[73] Assignee: Massachusetts Institute of Technology, Mass.

[21] Appl. No.: 604,142

[22] Filed: Oct. 26, 1990

[51] Int. Cl.$^5$ .............................................. A61B 5/04
[52] U.S. Cl. .................................................... 128/710
[58] Field of Search ............... 128/196, 710, 712, 731, 128/732, 733, 739, 740, 743, 784, 786

[56] References Cited

U.S. PATENT DOCUMENTS

| | | | |
|---|---|---|---|
| 3,294,084 | 12/1966 | Schuler et al. | 128/731 |
| 3,516,400 | 6/1970 | Krohn et al. | 128/695 |
| 3,707,147 | 12/1972 | Sellers | 128/712 |
| 3,717,141 | 2/1973 | Krohn et al. | 128/643 |
| 3,868,947 | 3/1975 | Holsinger | 128/639 |
| 4,346,715 | 8/1982 | Gammell | 128/804 |
| 4,417,591 | 11/1983 | Culver | 128/731 |
| 4,498,080 | 2/1985 | Culver | 128/731 |
| 4,517,983 | 5/1985 | Toyosu et al. | |
| 4,610,259 | 9/1986 | Cohen | 128/731 |
| 4,649,482 | 3/1987 | Raviv et al. | 364/417 |
| 4,736,751 | 4/1988 | Gevins et al. | 128/732 |
| 4,934,374 | 6/1990 | Ostlund et al. | 128/710 |
| 4,962,767 | 10/1990 | Brownlee | 128/696 |

OTHER PUBLICATIONS

Duffy et al. "Annals of Neurology", vol. 5, No. 4 Apr. 1979, pp. 309-320 (copy in file).
Estrin et al., "IEEE Transactions on Biomedical Engineering" vol. 16, No. 1, Jul. 1696, pp. 192-194 (copy in file).
Bourne et al. "Electroencephalography and Clinical Neurophysiology", vol. 30, 1971, pp. 423-436 (copy in file).
Galambos et al., "Cortical localization of pure tone responses using a Laplacian electrode", Federation Proceedings, 12, 48 (1953).
Hjorth, "An On-Line Transformation of EEG Scalp Potentials Into Orthogonal Source Derivations", Electroencephalography and Clinical Neurophysiology, 35, 526-530 (1975).
R. Srebro, "Localization of Visually Evoked Cortical Activity In Humans", J. Physiology, 360, 233-246 (1985).
F. Perrin et al., "Scalp Current Density Mapping: Value and Eximation from Potential Data", IEEE Transactions on Biomedical Engineering, 34, 283-288 Apr. 1987.
A. Gevins, "Analysis of the Electromagnetic Signals of the Human Brain: Milestones, Obstacles, and Goals", IEEE Transactions on Biomedical Engineering, 31, 833-850, Dec. 1984.
W. F. Poole et al., "Method for Modelling The Potential Sensed by a Concentric Multi-Ring Electrode Set from a Moving Depolarization Wave", IEEE Engineering In Medicine & Biology Society 11th Annual International Conf., 1297-1298 (1989).
R. M. Gulrajani et al., "The Inverse Problem In Electrocardiography: Solutions In Terms Of Equivalent Sources", Critical Reviews in Biomedical Engineering, 16, 171-214 (1988).
F. J. L. Van Capelle et al., "Conduction in Ischemic Myocardium", Normal and Abnormal Conduction in the Heart, A. P. de Carvalho et al., Editors, Futura Publishing Co., Mount Kisco, N.Y. (1982).

Primary Examiner—William E. Kamm
Attorney, Agent, or Firm—Choate, Hall & Stewart
(List continued on next page.)

[57] ABSTRACT

An array of electrodes is applied to an internal or external surface of a biological system such as a human being. The electrodes generate signals which are processed to compute a surface differential of the surface potential at a multiplicity of spatial locations within a given time epoch. The signal processing is repeated for multiple sequential time epochs and an image is constructed from the surface differential of the surface potential for each time epoch. Thereafter, the sequential images corresponding to sequential time epochs are displayed. The two-dimensional image changes as the distribution of bioelectric sources evolves so as to provide a motion picture of electrical activity.

67 Claims, 7 Drawing Sheets

OTHER PUBLICATIONS

Hjorth, "Source Derivation Simplifies Topographical EEG Interpretation", Am. J. EEG Technol., 20, 121–132 (1980).

"Relationship Between the Electrical Fields on the Body Surface During One Single Heart Beat and the Vector Loops, " by F.A.N. Kienle, Proceedings of the Satellite Symposium of the XXVth International Congress of Physiological Sciences, The Electrical Field of the Heart, and of the XIIth International Colloquium Vectorcardiographicum 1971: Presses Academiques Europeennes, Bruxelles, 1972, pp. 280–287.

"Das Elektrische Herzportrait, " Das Elektroanatomische Herzportrait, Das Elektrische Dynamishceh Herzportrait, Ein Bericht der vorligenden Forschungsergebnisse der Herzklinik Karlsruhe, Printed in Germany, Stand Jan. 1973, English language translations of the text relating to FIGS. 66 and 67 are enclosed.

METHOD AND APPARATUS FOR IMAGING ELECTRICAL ACTIVITY IN A BIOLOGICAL SYSTEM

BACKGROUND OF THE INVENTION

To diagnose abnormalities in certain organ systems, one optimally would want to know the electrical state of each region in the organ system at each instant in time. Example organ systems about which one would wish to know the electrical state include the heart, the brain, and skeletal muscles.

Previous investigators have attempted to localize electrical activity in the brain. See, F. H. Duffy, et al., "Brain Electrical Activity Mapping (BEAM): A Method for Extending the Clinical Utility of EEG and Evoked Potential Data," *Annals of Neurology*, 5, p. 309, 1979 and G. Raviv et al., U.S. Pat. No. 4,649,482. Their approach involves displaying on a video screen surface potentials recorded from multiple electrodes placed on the surface of the head. Galambos et al., "Cortical Localization of Pure Tone Responses Using a Laplacian Electrode," *Federation Proceedings*, 12, 48, 1953, reported using a set of five electrodes to compute the Laplacian of the surface potential at a single location on the scalp to localize brain responses to auditory tones. They did not generate images. Similarly, Hjorth in "An On-Line Transformation of EEG Scalp Potentials into Orthogonal Source Derivations," *Electroencephalography and Clinical Neurophysiology*, 35, 526–530, 1975, attempted to measure the Laplacian of the scalp surface potentials in order to localize brain electrical activity using nineteen widely spaced unipolar electrodes. He did not generate images. R. Srebro in "Localization of Visually Evoked Cortical Activity in Humans," *J. Physiology*, 360, 233–246, 1985 also localized cortical activity in the brain using a set of five electrodes (comprising the "Laplacian electrode"), to compute the Laplacian of the surface potential at a single site. He moved this set of electrodes to different sites and measured brain activity in response to visual stimulii. Because of poor signal to noise characteristics he measured only an average response to stimuli repeated 128 times. He did not localize spontaneous brain electrical activity. Srebro constructed a fixed image based on recordings from multiple placements of the Laplacian electrode. The physical separation of the electrodes was 2.5 cm yielding an effective "Laplacian electrode" diameter of 5 cm thereby providing only crude localization.

F. Perrin et al., "Scalp Current Density Mapping: Value and Estimation from Potential Data," *IEEE Transactions on Biomedical Engineering*, 34, 283–288, 1987, conducted a theoretical analysis of "scalp current density" which is proportional to the two-dimensional Laplacian of potentials measured on the scalp.

Gevins, in "Analysis of the Electromagnetic Signals of the Human Brain: Milestones, Obstacles and Goals," *IEEE Transactions on Biomedical Engineering*, 31, 833–850, 1984, discusses the improved spatial resolution that the Laplacian of surface potentials recorded from the head provides for identifying sources of brain electrical activity. Gevins indicates that if one uses an array of unipolar electrodes that the Laplacian cannot be computed at points corresponding to the periphery of the array. W. F. Poole et al. in "Method for Modelling the Potential Sensed by a Concentric Multi-Ring Electode Set from a Moving Depolarization Wave," IEEE EMBS 11th Annual International Conference, 1297–1298, 1989, simulate the signal sensed by concentric ring electrodes but no method or apparatus is proposed for using such electrodes to record and display images of bioelectrical sources in the body.

Previous investigators have also devoted effort to measuring cardiac electrical activity. As is well known, the cyclic process of electrical activation (depolarization) and deactivation (repolarization) of the heart muscle triggers the mechanical contraction and relaxation of the heart muscle. To diagnose abnormalities in cardiac electrical activity one would wish to know the electrical state of each region of myocardial tissue at each point in time. The standard clinical means of assessing abnormalities of cardiac electrical activity involves body surface electrocardiography. In this technique, one records the instantaneous electrical potential difference between two points on the body surface. This potential difference fluctuates in time due to the electrical activity of the heart. The interface between each region of depolarized and repolarized tissue generates an equivalent electric dipole. These electric dipoles cause currents to flow in the body which acts as a volume conductor. This process results in an electric potential distribution within the body and on the body surface. The electric potential distribution changes as the state of cardiac depolarization and repolarization evolves during the cardiac cycle.

Conventional electrocardiography involves displaying versus time the electrical potential difference for one or more pairs of electrodes on the body surface. For each pair of electrodes, one obtains a signal which for each point in time represents a summation of the contributions of all the spatially separated electric dipoles in the myocardium. By use of multiple pairs of electrodes, one can estimate the instantaneous magnitude of each of the three vector components of a net "cardiac dipole" located theoretically in the center of the heart. However, one may not localize spatially distributed dipole sources in the heart by means of conventional body surface electrocardiography.

Attempts have been made to obtain spatial information on cardiac electrical activity. One technique that has been used is body surface mapping in which a large number of electrodes are placed on the body surface (primarily on the torso) and contour maps of the potential distributions on the body surface are made at different time points during the cardiac cycle. Unfortunately, the ability to interpret these potential maps has been very poor in terms of identifying electric dipole source distributions within the heart. Thus, this technique has not been adapted into routine clinical practice.

An underlying problem in terms of determining electrical source distributions within the heart from body surface potentials is the non-uniqueness of the electrocardiograph inverse problem. One can show mathematically that even if one could measure the potential distribution arbitrarily accurately everywhere on the body surface, and one could assume uniform conductivity of the body contents, one could not uniquely determine the three-dimensional distribution of sources within the heart. See, R. M. Gulrajani et al., "The Inverse Problem in Electrocardiography: Solution in Terms of Equivalent Sources," *Critical Reviews in Biomedical Engineering*, 16, 171–214, 1988. Attempts at solving the ECG inverse problem by constraining the number and location of cardiac dipoles has also generally proved unsatisfactory.

Mapping of cardiac electrical activity can be performed in experimental animals or in patients by applying electrodes directly to the endocardial surface, epicardial surface, or in the myocardium itself by means of needle electrodes. This approach is highly invasive and suffers from the fact that the electrograms, especially those recorded from bipolar electrodes, represent electrical activity localized to the region of the electrodes. Thus, it is difficult to map conduction paths because one is recording only from a finite number of points and conduction may progress between recording sites. Further, conventional bipolar electrodes may impose a directional bias on the recordings. F. J. L. van Capelle et al., "Conduction in Ischemic Myocardium," *Normal and Abnormal Conduction in the Heart*, A. P. de Carvalho, B. F. Hoffman, and M. Lieberman, Eds., Futura Publishing, Mount Kisco, New York, 1982, recorded electrical potentials directly from the surface of the heart and computed the Laplacian of the array of electrodes. They reported a single "source current" map based on these measurements.

SUMMARY OF THE INVENTION

The method according to the invention for imaging electrical activity in a biological system includes applying an array of electrodes to an internal or external surface of the biological system to generate electrical signals. The signals from the electrodes are processed to compute a surface differential of the surface potential at a multiplicity of spatial locations substantially simultaneously, that is, within a given short time epoch. The process is repeated for multiple sequential time epochs and an image is constructed from the surface differential of the surface potential for each time epoch. Thereafter, sequential images corresponding to sequential time epochs are displayed. In a preferred embodiment, the surface differential of the surface potential is a two-dimensional Laplacian of the surface potential. In this embodiment, the two-dimensional Laplacian of the surface potential is obtained by utilizing bipolar electrodes consisting of an outer ring conductor and a separate central conductor. The electrical activity may originate in the heart, the brain, skeletal muscle or other organ systems.

Cardiac electrical activity may be imaged by applying an electrode array to the anterior chest wall overlying the heart, to the posterior chest wall overlying the heart, to the lateral chest wall overlying the heart or to combinations of these locations. Alternatively, cardiac electrical activity is imaged by applying an electrode array to the epicardial surface of the heart, or to the endocardial surface of the heart. The invention may also be practiced to image brain electrical activity by applying an electrode array to the surface of the head, or to the surface of the brain.

In any of these embodiments, the image is constructed from the surface differential of the surface potential. This image may be displayed on an array of pixels wherein the magnitude of the surface differential of the surface potential is encoded on a gray scale. Alternatively, the magnitude of the surface differential of the surface potential may be encoded on a color scale. In another embodiment, a smoothing and interpolation algorithm is applied to smooth the contours of the image and reduce pixel size. The method and apparatus of the invention may also be used to image skeletal muscle activity by applying an electrode array to the skin overlying the muscle.

In a preferred embodiment, the electrical signals are digitized and stored on a computer disk and the image is displayed in real time by displaying from eight to thirty-two frames per second. The images also may be displayed off-line from a computer disk at a rate slower than real time. It is also contemplated that individual frames may be examined one at a time.

According to another aspect of the invention, electrical activity is imaged by applying an array of electrodes to an external surface of the biological system. Signals from the electrodes are processed to compute a surface differential of the surface potential at a multiplicity of spatial locations substantially simultaneously and an image is constructed from the surface differential of the surface potential to image the electrical activity. This non-invasive aspect of the invention is effective nothwithstanding that electrical signals are an order of magnitude weaker at an external surface as compared with a surface of the organ itself.

The invention disclosed herein provides an important diagnostic tool with particular utility for imaging cardiac electrical activity. The non-invasive aspects of certain embodiments of the invention are particularly important. Since the electrical activity of the heart is so intimately related to its function, virtually all pathological processes involving the heart affect its electrical activity. Such pathological processes include abnormalities in cardiac electrical conduction processes and disturbances of heart rhythm (dysrhythmias), myocardial ischemia, myocardial infarction and alterations in chamber size and muscle mass. The ability to image cardiac electrical activity non-invasively with the present invention will bring the spatial dimension to the analysis of cardiac electrical activity. Clinical electrocardiography currently lacks the ability to resolve spatially distributed sources. The present invention will provide critically important information which is not presently available. For example, many rhythm disturbances involve the development of re-entrant loops of activity. These loops at present cannot be identified non-invasively. With the cardiac electrical imaging of the invention, these loops can be visualized and the ability of pharmacological agents to interfere with the formation of these loops can be directly assessed. The sites of abnormal impulse initiation (ectopic beats) within the heart could be directly localized. The present invention may also help in the placement of artificial pacemakers and their functioning may be assessed with greater accuracy and specificity.

Abnormalities of cardiac electrical conduction processes are a principal cause of morbidity and mortality in the developed world. Cardiac electrical imaging of the invention will enable physicians to diagnose abnormalities in cardiac conduction processes and non-invasively monitor and treat these abnormalities with precision. Beyond primary disturbances of electrical conduction processes, changes in cardiac electrical activity as represented by cardiac electrical imaging of this invention will enable one to diagnose other pathological conditions such as cardiac ischemia or infarction. Conventional electrocardiography is used to diagnose cardiac ischemia and infarction but is limited by its lack of sensitivity and spatial resolution. As a result, radionuclide scanning techniques are used to provide some spatial localization during exercise testing. The ability to correctly diagnose chest pain originating from ischemia or infarction is limited, necessitating the admission of many emergency room patients to coronary care units as a precautionary measure. The non-invasive cardiac electrical imaging of this invention will enable one to diagnose localized areas of ischemia or infarction with sensitivity and specificity providing more precise diagnoses and the ability to guide therapy. This technique would limit the need for expensive and inconvenient radioisotopic tests and enable physicians to hospitalize only those patients who actually require hospitalization for treatment. One could also utilize cardiac electrical mapping to monitor progression or regression of ischemia or extension of infarction in patients.

None of the references discussed above dealing with brain or cardiac imaging disclose creating and displaying sequential images computed from a surface differential of the surface potential at a multiplicity of spatial locations substantially simultaneously. It is this ability to map a surface differential of a surface potential at multiple locations substantially simultaneously and displaying of images for multiple sequential time epochs which advance the state of imaging of bioelectrical sources in organ systems.

DESCRIPTION OF THE PREFERRED EMBODIMENT

The present invention provides method and apparatus for imaging electrical activity from sources within an organ system either from body surface electrodes or from internal electrodes. This technique explicitly recognizes that one cannot uniquely reconstruct from a two-dimensional array of electrodes a three-dimensional distribution of sources. What the present invention does is to construct a two-dimensional image which is a type of projection of those sources onto a two-dimensional surface. In the cardiac context, this two-dimensional image changes as the distribution of sources evolves during the cardiac cycle and provides a kind of motion picture of cardiac electrical activity. The images generated by the present invention may be compared with the chest x-ray. The chest x-ray represents a two-dimensional projection of the anatomy of the chest. One cannot uniquely reconstruct the three-dimensional anatomy of the chest from the chest x-ray. Nonetheless, the chest x-ray is an extrordinarily important diagnostic tool in the diagnosis of pathology of the chest.

The basic theory of the present invention is based on fundamental electromagnetic theory applied to volume conductors. Under quasi-static conditions $$\nabla^2 \phi = \frac{-4\pi\rho}{\epsilon}$$

where $\nabla^2$ is the Laplacian operator in three dimensions, $\phi$ is the electric potential, $\rho$ is the charge density and $\epsilon$ is the permittivity. It can be shown that the charge density, $\rho$ is equivalent to the divergence of the impressed current $J_i$. See, R. Plonsey, "Laws governing Current Flow in the Volume Conductor" in *The Theoretical Basis of Electrocardiography*, C. V. Nelson and D. B. Geselwitz Eds., Claredon Press, Oxford 165–174, 1976. Consider an array of electrodes on a surface separated from an bioelectrical source $\rho$. Just inside the surface $\nabla^2\phi=0$. However, a two-dimensional (non-geometric) projection of the sources deep to the surface may be obtained by computing the two-dimensional Laplacian of $\phi$:

$$\frac{\partial^2 \phi}{\partial x^2} + \frac{\partial^2 \phi}{\partial y^2} = \frac{-4\pi}{\epsilon} \rho_{projected}.$$

Figure 1A:
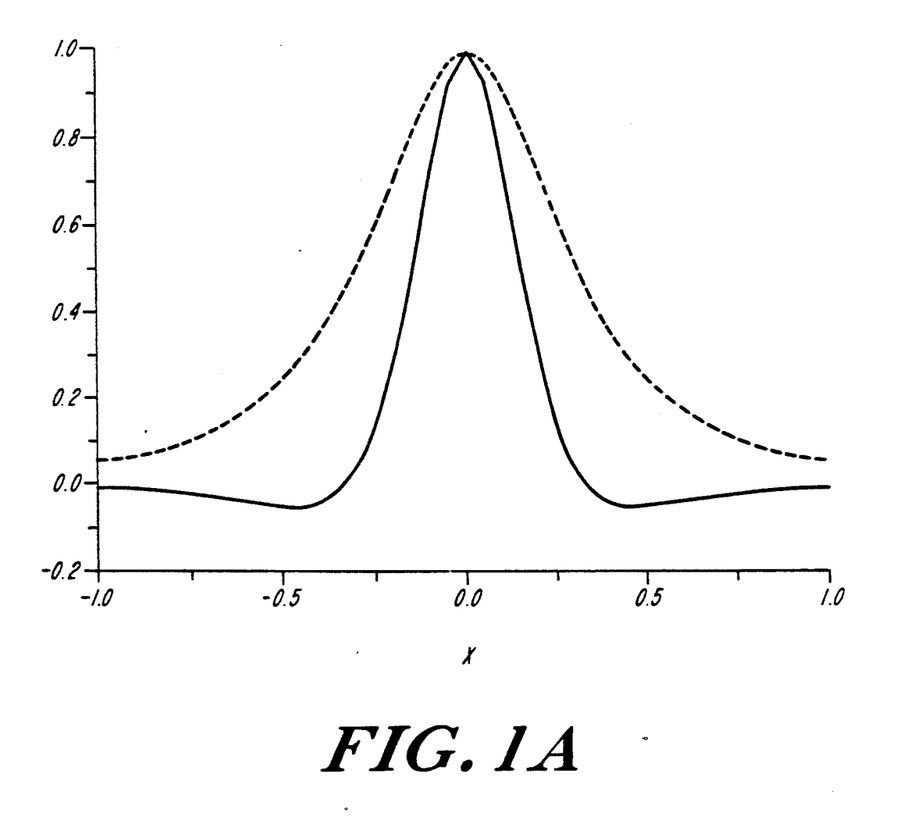
FIG. 1a is a graph of surface potential versus distance x and the two-dimensional Laplacian of the surface potential versus distance x for a dipole immersed in an isotropic volume conductor bounded by a planar surface. The dipole is oriented perpendicular to the surface and the x axis is parallel to the surface.
Figure 1B:
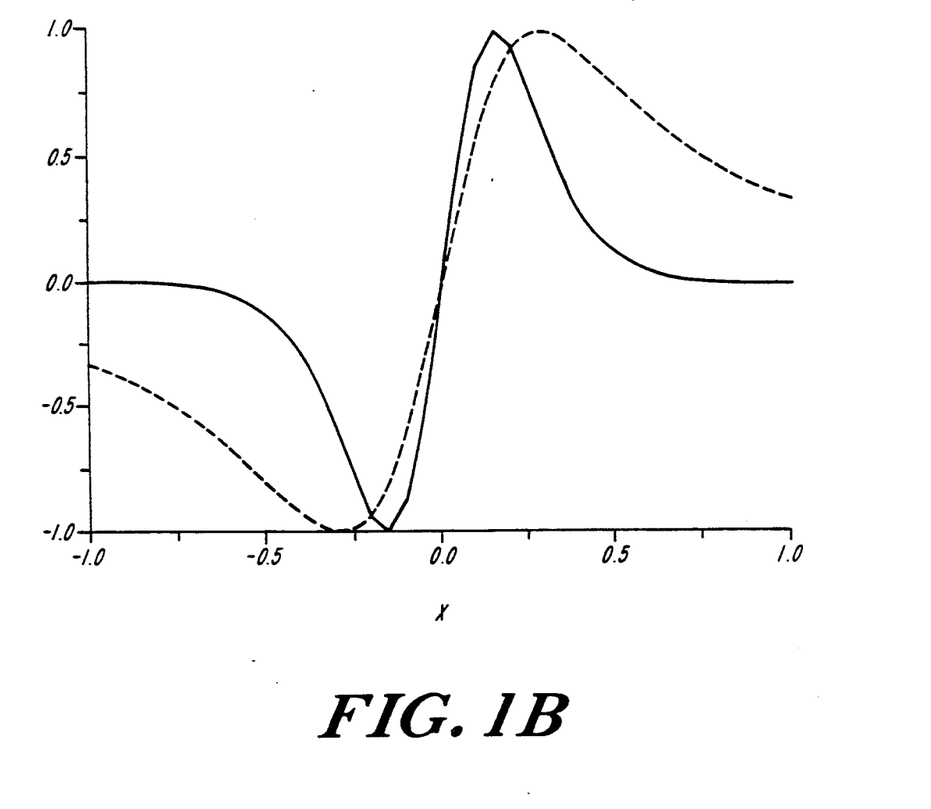
FIG. 1b is a graph of surface potential versus distance x and the two-dimensional Laplacian of the surface potential versus distance x for a dipole immersed in the isotropic volume conductor but now oriented along the x direction.

The plot of the two-dimensional Laplacian of $\phi$ yields a much sharper image of the source than does a plot of $\phi$ (x,y) itself. This is illustrated in FIGS. 1a and 1b in which the solid line represents a plot of the two-dimensional Laplacian of the surface potential versus x and the dotted line represents a plot of the surface potential $\phi$ itself versus distance. Thus, one can construct an image of cardiac electrical sources by computing and displaying suitably the two-dimensional Laplacian of the electric potential measured on a surface.

One could measure the two-dimensional Laplacian by setting up an M×N array of regularly spaced unipolar electrodes and estimating the two-dimensional Laplacian using an expression such as:

$$\left(\frac{\partial^2 \phi}{\partial x^2} + \frac{\partial^2 \phi}{\partial y^2}\right)_{i,j} \simeq \frac{1}{(DX)^2}[\phi_{i+1,j} + \phi_{i-1,j} - 2\phi_{i,j}] +$$

$$\frac{1}{(DY)^2}[\phi_{i,j+1} + \phi_{i,j-1} - 2\phi_{i,j}]$$

where $\phi_{i,j}$ is the potential at the electrode located at the point i·(DX)+J·(DY). In this example, however, the two-dimensional Laplacian would be determined only at (M−2)·(N−2) locations. Thus M·N electrodes and associated apparatus able to process M·N signals yield only (M−2)·(N−2) locations at which the two-dimensional Laplacian is measured. Also, under such conditions, noise in any one of the five electrodes used in a unipolar electrode array would corrupt the estimates of the two-dimensional Laplacian at a given location.

Figure 2:
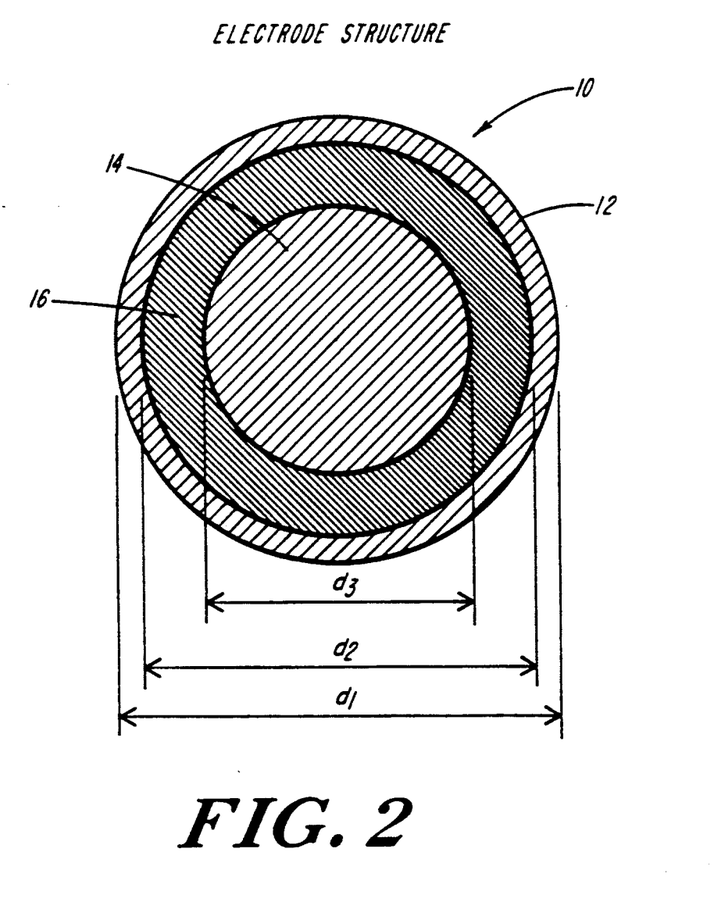
FIG. 2 is a cross-sectional view of a bipolar ring electrode.
Figure 3:
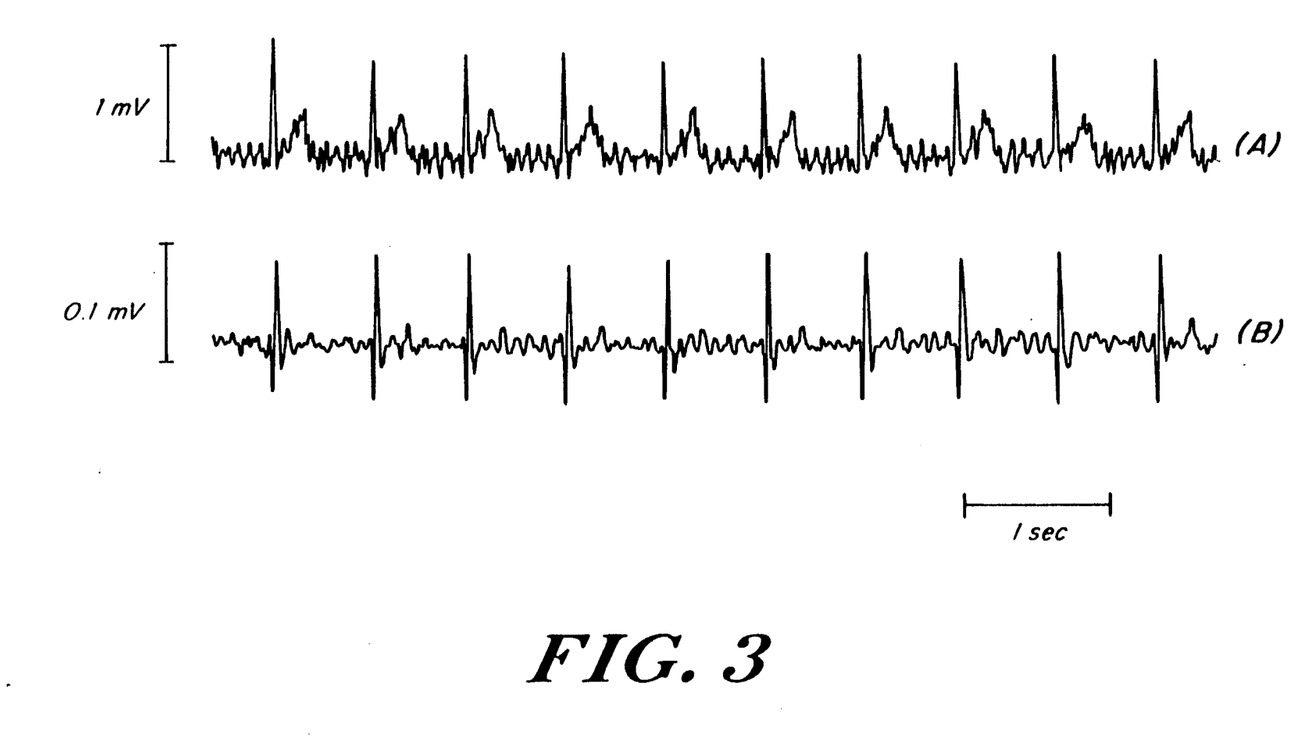
FIG. 3a is a plot versus time of the body surface potential measured between two electrodes corresponding to lead 1 of a standard electrocardiogram.
FIG. 3b is a plot of the corresponding signal measured from a bipolar ring electrode located on the left anterior chest wall.

An improved method for estimating the two-dimensional Laplacian involves using bipolar ring electrodes. With reference to FIG. 2, a bipolar ring electrode 10 includes an outer ring conductor 12 having an outer diameter d1 and an inner diameter d2. The outer ring conductor 12 surrounds an inner circular conductor 14 of diameter d3 separated by an insulator 16. The potential measured between the outer ring conductor 12 and the inner circular conductor 14 in the bipolar electrode 10 represents the two-dimensional Laplacian of the surface potential. An array of M·N bipolar electrodes and associated apparatus able to process M·N signals yield M·N locations at which the two-dimensional Laplacian is measured. Because signal-to-noise ratio may be higher for bipolar electrodes, the outer diameter of these electrodes can be smaller than for a "Laplacian electrode" constructed from a set of unipolar electrodes resulting in better localization. FIG. 3a is a plot versus time of the body surface potential measured between two electrodes corresponding to lead I of the standard electrocardiogram while FIG. 3b is a plot of the corresponding signal measured from a bipolar ring electrode located on the left anterior chest wall.

Although the analysis above might suggest that a two-dimensional Laplacian differential of the surface potentials is optimal, other surface differentials of the surface potential may be utilized. For example, a differential of the form $$\beta \frac{\partial^2 \phi}{\partial x^2} + (1 - \beta) \frac{\partial^2 \phi}{\partial y^2}$$

might account for nonisotropic conductivity (here $\beta$ lies between 0 and 1). Similarly, surface differentials including derivative orders other than two might be utilized.

Once an array of the two-dimensional Laplacian or other surface differentials of the surface potential is available, an image may be constructed. A simple way of displaying the image is to encode each signal from each electrode in the array on a gray scale or color scale. Each signal then corresponds to a pixel of the image. Suitable smoothing and interpolation algorithms can be used to smooth the image if desired.

Figure 4:
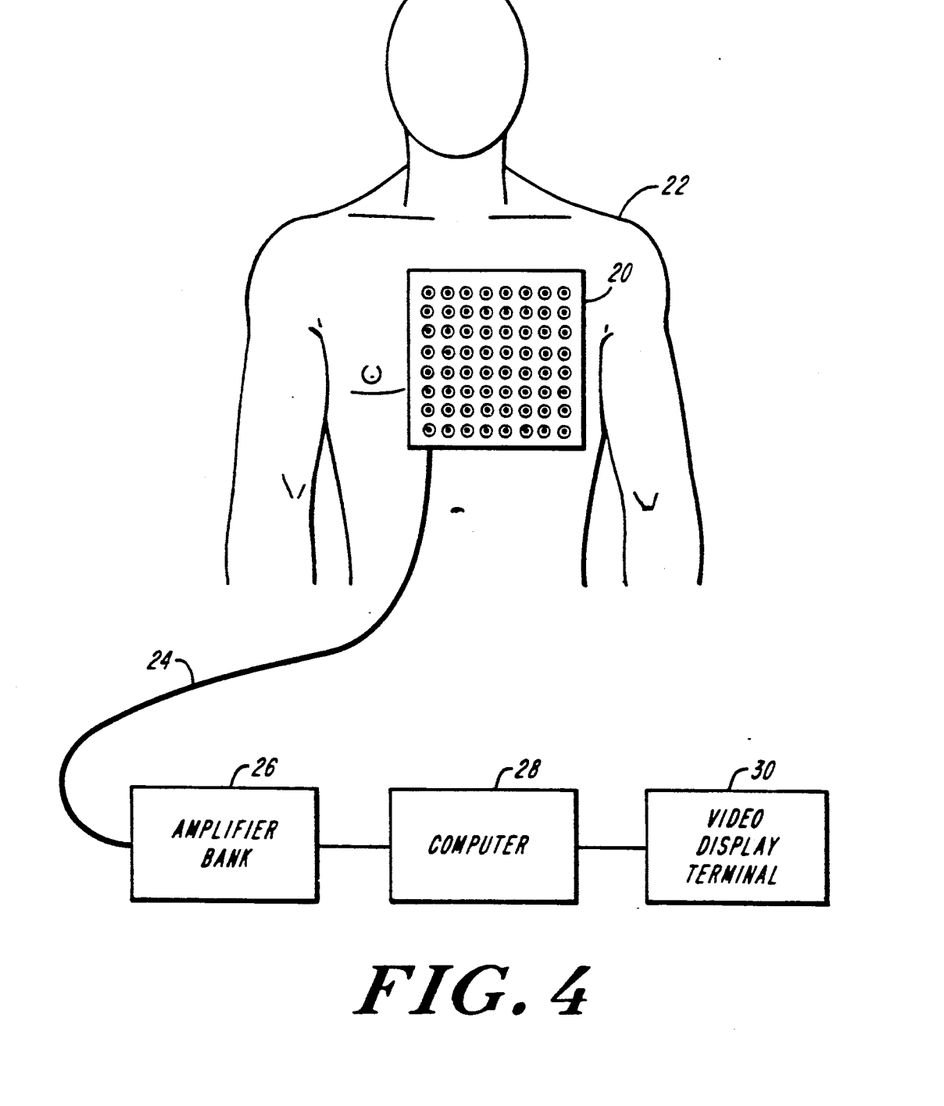
FIG. 4 is a schematic illustration of the apparatus according to the present invention.

A preferred embodiment of the invention for imaging cardiac electrical activity is shown in FIG. 4. An electrode pad 20 includes 64 bipolar electrodes 10 in an 8×8 array regularly spaced as shown. Each electrode 10 comprises a circular ring surrounding a circular electrode as shown in FIG. 2. In this embodiment, the outer diameter of the electrode 10 is 1.5cm and the spacing from the center of one electrode to the center of the next electrode is 2.5 cm. The pad may be placed over the anterior chest wall overlying the heart of a person 22. This placement will emphasize electrical sources located in the anterior portion of the heart. Placement of the pad 20 on the back of the chest overlying the heart will emphasize electrical sources located in the posterior of the heart. Placement of the pad 20 on the left lateral chest overlying the heart will emphasize sources located in the left lateral portion of the heart. Specialized pads could also be applied directly to the endocardial or epicardial surfaces of the heart.

Signals from the electrodes 10 of the electrode pad 20 are carried in a multi-lead cable 24 to an amplifier bank 26 where they are amplified and passed through anti-aliasing filters before being digitized at a rate of 1000 Hz per channel in a computer 28 equipped with a multiplexor and analog to digital conversion card. It is preferred that the digitized signals be stored in a storage medium such as a hard disk in the computer 28. The computer 28 also creates an electronic representation of images constructed from the signals from the electrode array 20. The constructed image is displayed on a video display terminal 30 by assigning each signal from the electrode array 20 to a square pixel approximately real size (e.g., 1.5 cm in diameter) in an 8×8 array. The voltages from the electrodes 10 in the electrode array 20 are all scaled and represented on a 64 level gray scale, the darkest level corresponding to maximal negative signal, the lightest level corresponding to maximal positive signal. Various smoothing and interpolation algorithms may be applied to smooth the contours of the image and reduce pixel size by an order of magnitude or more in linear dimension. The video images on the video display terminal 30 may be viewed in real time by displaying between 8 to 32 evenly spaced frames per second. To obtain finer temporal resolution, the frames may be displayed off-line from storage at a rate slower than real time, e.g., frames obtained every millisecond could be displayed at a rate of 16 frames per second. The data may be off-loaded from the hard disk onto digital tape or optical disk for long term storage if desired. To improve spectral resolution, electrode pads of 256 or even 1,024 electrodes may be desirable. In such cases, the electrodes would need to be made smaller, e.g., 0.75 or 0.375 cm in diameter, respectively. It will be readily apparent that the electrode pad 20 may be applied to the head or to skin overlying skeletal muscles for imaging electrical activity from those organs. As used in this application, the surface differential of the surface potential is a function involving derivatives of the surface potential with respect to coordinates along the surface. Also as used herein, the phrase "sequential time epochs" does not necessarily imply immediately successive epochs.

Figure 5A:
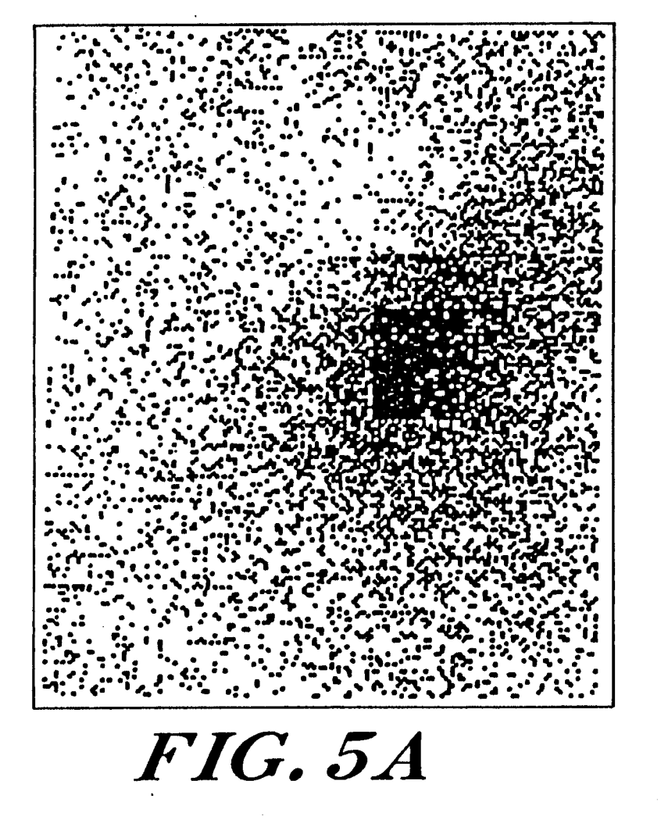
FIG. 5a is an image of body surface potential distribution.
Figure 5B:
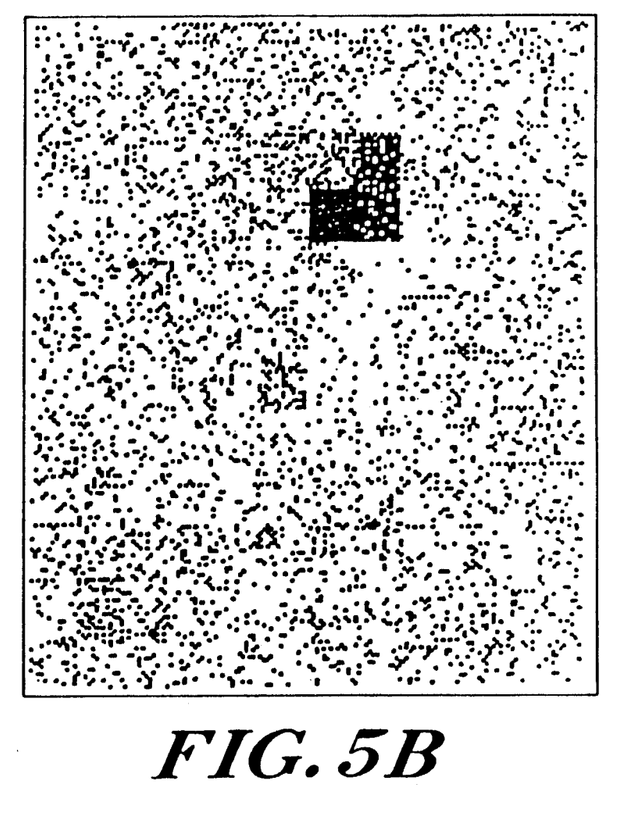
FIG. 5b is an image of the two-dimensional Laplacian of the body surface potential.

An example of the improved resolution provided by the present method as applied to an array of unipolar recordings is shown in FIGS. 5a and 5b shows the body surface potential on the anterior chest plotted on a gray scale during one point in time during the QRS complex. In comparison, FIG. 5b demonstrates the two-dimensional Laplacian of this potential indicating that a highly localized source distribution is responsible for generating the entire rather diffuse body surface potential of FIG. 5a.

In FIG. 5a, an array of unipolar electrodes was applied to the anterior chest. The signal from each unipolar electrode was associated with a gray scale and the gray scale level displayed at a pixel location on a display corresponding to the location of the unipolar electrode. For comparison in FIG. 5b, the signals from the unipolar array were used to compute the two-dimensional Laplacian of the surface potential as discussed above and the Laplacian is associated with a gray level scale for the corresponding pixel.

Figure 6:
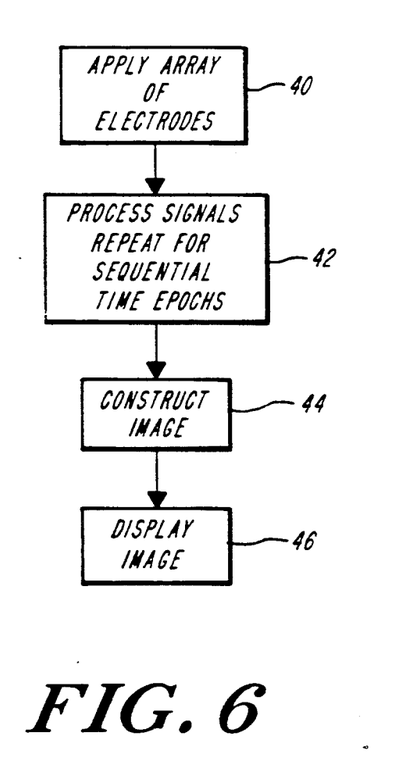
FIG. 6 is a block diagram of the method of the invention.

FIG. 6 is a block diagram illustrating the method of the invention. In step 40, an array of electrodes is applied to an internal or external surface of a biological system. Signals from the array of electrodes is processed in processing apparatus 42 and the processing is repeated for sequential time epochs. The processed signals are used to construct an image 44 and the image is displayed in a display device 46. The image 44 may be constructed, for example, by assigning each signal from the array to a square pixel in a display device. The image may be displayed using a gray scale or a color scale. Further, conventional smoothing algorithms may be used to smooth contours of the image and to reduce pixel size.

What is claimed is:

1. Method for imaging electrical activity in a biological system comprising:
   applying an array of electrodes to a surface of the biological system to generate signals;
   processing the signals from the electrodes to compute a surface differential of the surface potential at a multiplicity of spatial locations within a given time epoch;
   repeating the processing for multiple sequential time epochs;
   constructing a two-dimensional projection image of the electrical activity from the surface differential of the surface potential for sequential time epochs; and
   displaying sequential images corresponding to sequential time epochs.

2. The method of claim 1 wherein the surface differential of the surface potential is a two-dimensional Laplacian of the surface potential.

3. The method of claim 2 wherein the electrodes in the array of electrodes in the applying step are bipolar having an outer ring conductor and a separate central conductor, whereby the two-dimensional Laplacian of the surface potential is obtained.

4. The method of claim 1 or 3 wherein the electrical activity imaged in the constructing step originates in the heart.

5. The method of claim 1 wherein the electrical activity imaged in the constructing step originates in the brain.

6. The method of claim 1 wherein the electrical activity imaged in the constructing step originates in skeletal muscle.

7. The method of claim 4 wherein cardiac electrical activity is imaged by applying the electrode array in the applying step to the anterior chest wall overlying the heart.

8. The method of claim 1 wherein cardiac electrical activity is imaged by applying the electrode array in the applying step to the posterior chest wall overlying the heart.

9. The method of claim 4 wherein the cardiac electrical activity is imaged by applying the electrode array in the applying step to the lateral chest wall overlying the heart.

10. The method of claim 4 wherein cardiac electrical activity is imaged by applying the electrode array in the applying step to the epicardial surface of the heart.

11. The method of claim 4 wherein cardiac electrical activity is imaged by applying the electrode array in the applying step to the endocardial surface of the heart.

12. The method of claim 5 wherein brain electrical activity is imaged by applying the electrode array in the applying step to the surface of the head.

13. The method of claim 5 wherein brain electrical activity is imaged by applying the electrode array in the applying step to the surface of the brain.

14. The method of claim 1 wherein the image is displayed in the displaying step on an array of pixels wherein the magnitude of the surface differential of the surface potential is encoded on a gray scale.

15. The method of claim 1 wherein the image is displayed in the displaying step on an array of pixels wherein the magnitude of the surface differential of the surface potential is encoded on a color scale.

16. The method of claim 1 wherein the processing step further includes application of a smoothing and interpolation algorithm applied to smooth contours of the image and to reduce pixel size.

17. The method of claim 6 wherein skeletal muscle electrical activity is imaged in the constructing step by applying an electrode array on the skin overlying the muscle.

18. The method of claim 1 wherein the signals recorded from the electrodes are digitized and stored.

19. The method of claim 1 wherein the images are displayed in the displaying step in real time by displaying 8 to 32 frames per second.

20. The method of claim 1 wherein the images are displayed in the displaying step off-line at a rate slower than real time.

21. Apparatus for imaging electrical activity in a biological system comprising:
    an array of electrodes adapted to be applied to a surface of the biological system;
    apparatus for processing the signals from the electrodes to compute a surface differential of the surface potential at a multiplicity of spatial locations within a given time epoch and repeating this processing for multiple sequential time epochs, the apparatus further adapted to construct a two-dimensional projection image of the electrical activity from the surface differential of the surface potential for sequential time epochs; and
    display apparatus for displaying sequential images corresponding to sequential time epochs.

22. The apparatus of claim 21 wherein the surface differential of the surface potentials is a two-dimensional Laplacian of the surface potential.

23. The apparatus of claim 22 wherein the electrodes in the array are bipolar having an outer ring conductor and a separate central conductor.

24. The apparatus of claim 21 or 23 wherein the electrical activity imaged originates in the heart.

25. The apparatus of claim 21 wherein the electrical activity imaged originates in the brain.

26. The apparatus of claim 21 wherein the electrical activity imaged originates in skeletal muscle.

27. The apparatus of claim 24 wherein cardiac electrical activity is imaged by applying the electrode array to the anterior chest wall overlying the heart.

28. The apparatus of claim 24 wherein cardiac electrical activity is imaged by applying the electrode array to the posterior chest wall overlying the heart.

29. The apparatus of claim 24 wherein cardiac electrical activity is imaged by applying the electrode array to the lateral chest wall overlying the heart.

30. The apparatus of claim 24 wherein cardiac electrical activity is imaged by applying the electrode array to the epicardial surface of the heart.

31. The apparatus of claim 24 wherein cardiac electrical activity is imaged by applying the electrode array to the endocardial surface of the heart.

32. The apparatus of claim 25 wherein brain electrical activity is imaged by applying the electrode array to the surface of the head.

33. The apparatus of claim 25 wherein brain electrical activity is imaged by applying the electrode array to the surface of the brain.

34. The apparatus of claim 21 wherein the image is displayed on an array of pixels wherein the magnitude of the surface differential of the surface potential is encoded on a gray scale.

35. The apparatus of claim 21 wherein the image is displayed on an array of pixels wherein the magnitude of the differential of the surface potential is encoded on a color scale.

36. The apparatus of claim 21 wherein a smoothing and interpolation algorithm is applied to smooth the contours of the image.

37. The apparatus of claim 21 wherein skeletal muscle electrical activity is imaged by applying the electrode array to skin overlying the muscle.

38. The apparatus of claim 21 wherein the digitized signals are stored in a storage medium.

39. The apparatus of claim 21 wherein the image is displayed in real time by displaying 8 to 32 frames per second.

40. The apparatus of claim 21 wherein the images are displayed off-line from a storage medium at a rate slower than real time.

41. Method for imaging electrical activity in a biological system comprising:
    applying an array of electrodes to an external surface of the biological system;
    processing the signals recorded from the electrodes to compute a surface differential of the surface potential at a multiplicity of spatial locations substantially simultaneously; and
    constructing a two-dimensional projection image of the electrical activity from the surface differential of the surface potential.

42. The method of claim 41 wherein the electrical activity imaged in the constructing step originates in the heart.

43. The method of claim 41 wherein the electrical activity imaged in the constructing step originates in the brain.

44. The method of claim 41 wherein the electrical activity imaged in the constructing step originates in skeletal muscle.

45. The method of claim 41 or 42 wherein the surface differential of the surface potential is a two-dimensional Laplacian of the surface potential.

46. The method of claim 45 wherein the electrodes in the array of electrodes in the applying step are bipolar having an outer ring conductor and a separate central conductor whereby the two-dimensional Laplacian of the surface potential is obtained.

47. Apparatus for imaging electrical activity in a biological system comprising:
    an array of electrodes for application to an external surface of the biological system;
    apparatus for processing the signals from the electrodes to compute a surface differential of the surface potential at a multiplicity of spatial locations substantially simultaneously; and
    apparatus for constructing an image from the surface differential of the surface potential.

48. The apparatus of claim 47 wherein the surface differential of the surface potential is a two-dimensional Laplacian of the surface potential.

49. The apparatus of claim 48 wherein the electrodes in the array are bipolar having an outer ring conductor and a separate central conductor.

50. The method of claim 1 wherein the displaying step of the sequential images creates a motion picture.

51. The method of claim 1 wherein the sequential images in the displaying step are displayed one at a time.

52. The apparatus of claim 21 wherein sequential images in the displaying step may be displayed to create a motion picture.

53. The apparatus of claim 21 wherein sequential images in the displaying step may be displayed one at a time.

54. Method for imaging electrical activity originating in a heart comprising:
    applying an array of electrodes to a surface for receiving electrical signals from the heart;
    processing the signals from the electrodes to compute a surface differential of the surface potential at a multiplicity of spatial locations within a given time epoch;
    repeating the processing for multiple sequential time epochs;
    constructing an image from the surface differential of the surface potential for sequential time epochs; and
    displaying the sequential images corresponding to sequential time epochs.

55. Apparatus for imaging electrical activity originating in a heart comprising:
    an array of electrodes adapted to be applied to a surface for receiving electrical signals from the heart;
    apparatus for processing the signals from the electrodes to compute a surface differential of the surface potential at a multiplicity of spatial locations within a time epoch and repeating this processing for multiple sequential time epochs, the apparatus further adapted to construct an image from the surface differential of the surface potential for sequential time epochs; and
    display apparatus for displaying sequential images corresponding to sequential time epochs.

56. Method for imaging electrical activity originating in a heart comprising:
    applying an array of electrodes to an external surface;
    processing the signals recorded from the electrodes to compute a surface differential of the surface potential at a multiplicity of spatial locations substantially simultaneously; and
    constructing an image from the surface differential of the surface potential.

57. Apparatus for imaging electrical activity originating in a heart comprising;
    an array of electrodes adapted to be applied to an external surface;
    apparatus for processing the signals from the electrodes to compute a surface differential of the surface potential at a multiplicity of spatial locations substantially simultaneously; and
    apparatus for constructing an image from the surface differential of the surface potential.

58. Method for recording electrical activity on a surface comprising:
    applying an array of bipolar electrodes to a surface, the electrodes having an outer ring conductor and a separate central conductor whereby the two-dimensional Laplacian of the surface potential is obtained.

59. The method of claim 1 or 4 or 41 or 46 or 54 or 56 further comprising the step of identifying reentrant loops of activity.

60. The method of claim 1 or 4 or 41 or 46 or 54 or 56 further comprising the step of localizing sites of abnormal impulse initiation.

61. The method of claim 1 or 4 or 41 or 46 or 54 or 56 further comprising the step of diagnosing localized areas of ischemia.

62. The method of claim 1 or 4 or 41 or 46 or 54 or 56 further including the step of diagnosing localized areas of infarction.

63. The method of claim 1 or 4 or 41 or 46 or 54 or 56 further including the step of using the image to guide the placement of an artificial pacemaker.

64. The method of claim 1 or 4 or 41 or 46 or 54 or 56 comprising the further step of assessing the functioning of artificial pacemakers.

65. The method of claim 1 or 4 or 41 or 46 or 54 or 56 comprising the further step of diagnosing abnormalities in cardiac conduction processes.

66. The method of claim 1 or 4 or 41 or 46 or 54 or 56 further comprising the step of noninvasively monitoring abnormalities in cardiac conduction processes.

67. The method of claim 1 or 4 or 41 or 46 or 54 or 56 further comprising the step of treating abnormalities in cardiac conduction processes.

* * * * *

UNITED STATES PATENT AND TRADEMARK OFFICE
CERTIFICATE OF CORRECTION

PATENT NO. : 5,146,926
DATED : September 15, 1992
INVENTOR(S) : Richard J. Cohen It is certified that error appears in the above-indentified patent and that said Letters Patent is hereby corrected as shown below:

Column 8, line 37: after 5b insert ". Fig. 5a"; and

Signed and Sealed this

Seventh Day of December, 1993

Attest:

BRUCE LEHMAN

Attesting Officer     Commissioner of Patents and Trademarks